United States Patent
Heckroth et al.

(10) Patent No.: US 9,254,347 B2
(45) Date of Patent: Feb. 9, 2016

(54) TISSUE ADHESIVE WITH ACCELERATED CURING

(75) Inventors: Heike Heckroth, Odenthal (DE); Christoph Eggert, Köln (DE)

(73) Assignee: Medical Adhesive Revolution GmbH, Aachen (DE)

( * ) Notice: Subject to any disclaimer, the term of this patent is extended or adjusted under 35 U.S.C. 154(b) by 197 days.

(21) Appl. No.: 14/112,132

(22) PCT Filed: Apr. 17, 2012

(86) PCT No.: PCT/EP2012/057019
§ 371 (c)(1),
(2), (4) Date: Nov. 13, 2013

(87) PCT Pub. No.: WO2012/143358
PCT Pub. Date: Oct. 26, 2012

(65) Prior Publication Data
US 2014/0066981 A1   Mar. 6, 2014

(30) Foreign Application Priority Data

Apr. 19, 2011  (EP) .................................. 11162944

(51) Int. Cl.
| C08G 18/32 | (2006.01) |
| C08G 18/38 | (2006.01) |
| C08G 18/10 | (2006.01) |
| A61L 24/04 | (2006.01) |
| A61B 17/03 | (2006.01) |
| C09J 175/02 | (2006.01) |
| A61M 5/19 | (2006.01) |
| C08G 18/12 | (2006.01) |
| C08G 18/73 | (2006.01) |
| A61L 24/00 | (2006.01) |
| A61B 17/00 | (2006.01) |

(52) U.S. Cl.
CPC ......... *A61L 24/046* (2013.01); *A61B 17/00491* (2013.01); *A61L 24/0015* (2013.01); *A61M 5/19* (2013.01); *C08G 18/10* (2013.01); *C08G 18/12* (2013.01); *C08G 18/325* (2013.01); *C08G 18/3821* (2013.01); *C08G 18/73* (2013.01); *C09J 175/02* (2013.01); *A61B 2017/00495* (2013.01)

(58) Field of Classification Search
IPC ........... A61B 17/00491; A61L 24/046,24/0015; A61M 5/19; C08G 18/12, 18/10, 18/3821, C08G 18/73, 18/325; C08L 75/02; C09J 175/02
See application file for complete search history.

(56) References Cited

U.S. PATENT DOCUMENTS

| 3,158,635 | A | * | 11/1964 | Kezerian et al. ............... 562/565 |
| 3,979,442 | A | * | 9/1976 | Schafer et al. ................. 560/169 |
| 4,705,889 | A | * | 11/1987 | Hendricks et al. ............. 562/564 |
| 7,754,782 | B2 | * | 7/2010 | Heckroth et al. .............. 523/111 |
| 9,051,410 | B2 | * | 6/2015 | Heckroth et al. ..................... 1/1 |
| 2008/0145696 | A1 | * | 6/2008 | Senkfor et al. ................. 428/687 |
| 2011/0123479 | A1 | | 5/2011 | Heckroth et al. |
| 2012/0178847 | A1 | | 7/2012 | Heckroth et al. |

FOREIGN PATENT DOCUMENTS

| EP | 2145634 A1 | 1/2010 |
| EP | 2275466 A1 | 1/2011 |

OTHER PUBLICATIONS

International Search Report for PCT/EP2012/057019 mailed Sep. 19, 2012.

* cited by examiner

*Primary Examiner* — Rabon Sergent
(74) *Attorney, Agent, or Firm* — Drinker Biddle & Reath LLP

(57) ABSTRACT

The present invention relates to a polyurea system encompassing as component A) isocyanate-functional prepolymers obtainable by reaction of aliphatic isocyanates A1) with polyols A2), which can in particular have a number average molecular weight of ≥400 g/mol and an average OH functionality of 2 to 6, as component B) amino-functional compounds of general formula (I) in which X is an organic residue comprising a tertiary amino function, having no Zerewitinoff active hydrogen, $R_1$ is a $CH_2$—$COOR_3$ residue, in which $R_3$ is an organic residue having no Zerewitinoff active hydrogen, a linear or branched C1 to C4 alkyl residue, a cyclopentyl or cyclohexyl residue or H, $R_2$ is an organic residue having no Zerewitinoff active hydrogen, n is an integer ≥2 or ≤3, in particular for closing, binding, bonding or covering cell tissue, and to a metering system for the polyurea system according to the invention.

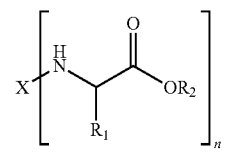

10 Claims, No Drawings

TISSUE ADHESIVE WITH ACCELERATED CURING

RELATED APPLICATIONS

This application is a national stage application (under 35 U.S.C. §371) of PCT/EP2012/057019, filed Apr. 17, 2012, which claims benefit of European Application No. 11162944.0, filed Apr. 19, 2011, which is incorporated by reference herein.

The present invention relates to a polyurea system, particularly for closing, binding, bonding or covering cell tissue, and to a metering system for the polyurea system according to the invention.

Various materials that are used as tissue adhesives are commercially available. These include the cyanoacrylates Dermabond® (octyl 2-cyanoacrylate) and Histoacryl Blue® (butyl cyanoacrylate). However, dry substrates are a prerequisite for efficient bonding by cyanoacrylates. In the case of heavy bleeding, adhesives of this type fail.

As an alternative to the cyanoacrylates, biological adhesives, such as e.g. BioGlue®, a mixture of glutaraldehyde and bovine serum albumin, various collagen- and gelatine-based systems (FloSeal®) and the fibrin adhesives (Tissucol), are available. These systems are primarily used to stop bleeding (haemostasis). Apart from the high costs, fibrin adhesives are distinguished by relatively weak adhesive strength and rapid degradation, so that they can only be used for minor injuries on tissue that is not under tension. Collagen- and gelatine-based systems, such as FloSeal®, are used exclusively for haemostasis. In addition, since fibrin and thrombin are obtained from human material and collagen and gelatine from animal material, there is always the risk of infection in biological systems. Biological materials must also be kept refrigerated, so that use in emergency medical care, such as e.g. in disaster areas, for military operations etc., is not possible. For the treatment of traumatic wounds here, QuikClot® or QuikClot ACS+™ is available, which is a granulated mineral that is applied into the wound in an emergency and leads to clotting there by dehydration. In the case of QuikClot®, this is a strongly exothermic reaction which leads to burning. QuikClot ACS+™ is a gauze into which the salt is embedded. The system has to be pressed firmly on to the wound to stop bleeding.

From EP 2 275 466 A1, the production and use of polyurea systems as tissue adhesives is known. The systems disclosed here encompass an amino-functional aspartic acid ester and an isocyanate-functional prepolymer. In addition, a tertiary amine is comprised. This is used to increase the rate of curing of the polyurea system, since this is of considerable importance, particularly when it is used to stop bleeding. The polyurea systems described can be used as tissue adhesives for closing wounds in human and animal cell structures. A very good bonding result can be achieved therewith.

However, with the systems described in EP 2 275 466 A1 there is the risk that at least some of the amines used to accelerate the curing can be eluted in the body. This can result in undesirable biological effects.

The object of the invention was therefore to provide a polyurea system with a particularly high rate of curing in which there is no risk of a release of amines in the body.

This object is achieved according to the invention by a polyurea system encompassing
as component A) isocyanate-functional prepolymers obtainable by reaction of
aliphatic isocyanates A1) with
polyols A2), which can in particular have a number average molecular weight of ≥400 g/mol and an average OH functionality of 2 to 6,
as component B) amino-functional compounds of general formula (I)

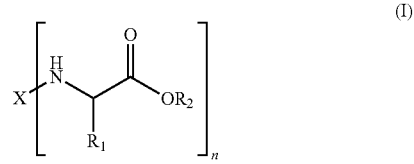

in which
X is an organic residue comprising a tertiary amino function, having no Zerewitinoff active hydrogen,
$R_1$ is a $CH_2$—$COOR_3$ residue, in which $R_3$ is an organic residue having no Zerewitinoff active hydrogen, a linear or branched C1 to C4 alkyl residue, a cyclopentyl or cyclohexyl residue or H,
$R_2$ is an organic residue having no Zerewitinoff active hydrogen,
n is 2 or 3.

The polyurea system according to the invention is distinguished by a very high rate of curing, which makes it particularly suitable for haemostasis. Since the system according to the invention also comprises no low molecular weight amines that are not incorporated into the polymer network, there is also no risk that these compounds could be eluted and thus released in the body.

For the definition of Zerewitinoff active hydrogen, reference is made to Römpp Chemie Lexikon, Georg Thieme Verlag Stuttgart. Groups with Zerewitinoff active hydrogen are preferably understood to be OH, NH or SH.

According to a preferred embodiment of the polyurea system according to the invention, X is a residue of formula (II)

in which
$R_4$, $R_5$, $R_6$ are, each independently of one another, an organic residue having no Zerewitinoff active hydrogen.

It is particularly preferred here if $R_4$, $R_5$, $R_6$ are, each independently of one another or simultaneously, a linear or branched, saturated organic residue that is optionally also substituted in the chain with heteroatoms, in particular a linear or branched, saturated, aliphatic C1 to C10, preferably C2 to C8 and particularly preferably C2 to C6 hydrocarbon residue.

Most particularly preferably, $R_4$, $R_5$, $R_6$ are, each independently of one another or simultaneously, a methyl, ethyl, propyl or butyl residue.

A polyurea system encompassing a compound of formula (I) in which the residues $R_1$, $R_2$ and optionally $R_3$ are, each independently of one another or simultaneously, a linear or branched C1 to C10, preferably C1 to C8, particularly preferably C2 to C6, most particularly preferably C2 to C4 organic residue and in particular an aliphatic hydrocarbon residue, is also advantageous. Examples of particularly suitable residues are methyl, ethyl, propyl and butyl.

The isocyanate-functional prepolymers A) are obtainable by reaction of polyisocyanates A1) with polyols A2) with the optional addition of catalysts as well as auxiliary substances and additives.

As polyisocyanates A1), for example monomeric aliphatic or cycloaliphatic di- or triisocyanates, such as 1,4-butylene diisocyanate (BDI), 1,6-hexamethylene diisocyanate (HDI), isophorone diisocyanate (IPDI), 2,2,4- and/or 2,4,4-trimethylhexamethylene diisocyanate, the isomeric bis(4,4'-isocyanatocyclohexyl)methanes or mixtures thereof with any isomer content, 1,4-cyclohexylene diisocyanate, 4-isocyanatomethyl-1,8-octane diisocyanate (nonane triisocyanate), 2-isocyanatoethyl 6-isocyanatocaproate, and alkyl 2,6-diisocyanatohexanoate (lysine diisocyanate) with C1-C8 alkyl groups, can be used.

In addition to the above-mentioned monomeric polyisocyanates A1), their higher molecular-weight secondary products with uretdione, isocyanurate, urethane, allophanate, biuret, iminooxadiazinedione or oxadiazinetrione structure and mixtures thereof can be used.

It is preferred to use polyisocyanates A1) of the above type with exclusively aliphatically or cycloaliphatically bound isocyanate groups or mixtures thereof.

It is also preferred if polyisocyanates A1) of the above type having an average NCO functionality of 1.5 to 2.5, preferably of 1.6 to 2.4, more preferably of 1.7 to 2.3, most particularly preferably of 1.8 to 2.2 and in particular of 2, are used.

Most particularly preferably, hexamethylene diisocyanate is used as polyisocyanate A1).

According to another preferred embodiment of the polyurea system according to the invention, it is provided that the polyols A2) are polyester polyols and/or polyester-polyether polyols and/or polyether polyols. Particularly preferred here are polyester-polyether polyols and/or polyether polyols with an ethylene oxide content of between 60 and 90 wt. %.

It is also preferred if the polyols A2) have a number average molecular weight of 4000 to 8500 g/mol.

Suitable polyether-ester polyols are produced according to the prior art preferably by polycondensation from polycarboxylic acids, anhydrides of polycarboxylic acids, as well as esters of polycarboxylic acids with volatile alcohols, preferably C1 to C6 monools, such as methanol, ethanol, propanol or butanol, with a molar excess of low molecular weight and/or higher molecular weight polyol, polyols comprising ether groups being used as polyol, optionally in mixtures with other, ether group-free, polyols.

It is, of course, also possible to use mixtures of higher molecular weight and low molecular weight polyols for polyether-ester synthesis.

These low molecular weight polyols in molar excess are polyols with molar masses of 62 to 299 daltons, with 2 to 12 C atoms and hydroxyl functionalities of at least 2, which can furthermore be branched or unbranched and the hydroxyl groups of which are primary or secondary. These low molecular weight polyols can also comprise ether groups. Typical representatives are ethylene glycol, 1,2-propanediol, 1,3-propanediol, 1,4-butanediol, 2,3-butanediol, 2-methyl-1,3-propanediol, 1,5-pentanediol, 1,6-hexanediol, 3-methyl-1,5-pentanediol, 1,8-octanediol, 1,10-decanediol, 1,12-dodecanediol, cyclohexanediol, diethylene glycol, triethylene glycol and higher homologs, dipropylene glycol, tripropylene glycol and higher homologs, glycerol, 1,1,1-trimethylolpropane, as well as oligotetrahydrofurans with hydroxyl end groups. It is, of course, also possible to use mixtures within this group.

Higher molecular weight polyols in molar excess are polyols with molar masses of 300 to 3000 daltons, which can be obtained by ring-opening polymerisation of epoxides, preferably ethylene and/or propylene oxide, and by acid-catalysed, ring-opening polymerisation of tetrahydrofuran. For the ring-opening polymerisation of epoxides, either alkali hydroxides or double metal cyanide catalysts can be used.

As a starter for ring-opening epoxide polymerisations, all at least bifunctional molecules from the group of the amines and the above-mentioned low molecular weight polyols can be used. Typical representatives are 1,1,1-trimethylolpropane, glycerol, o-TDA, ethylenediamine, 1,2-propylene glycol, etc. as well as water, including mixtures thereof. It is, of course, also possible to use mixtures within the group of the excess higher molecular weight polyols.

The synthesis of the higher molecular weight polyols, insofar as they are hydroxyl group-terminated polyalkylene oxides of ethylene and/or propylene oxide, can take place randomly or blockwise, in which case mixed blocks can also be comprised.

Polycarboxylic acids are both aliphatic and aromatic carboxylic acids, which can be either cyclic, linear, branched or unbranched and can have between 4 and 24 C atoms.

Examples are succinic acid, glutaric acid, adipic acid, azelaic acid, sebacic acid, 1,10-decanedicarboxylic acid, 1,12-dodecanedicarboxylic acid, phthalic acid, terephthalic acid, isophthalic acid, trimellitic acid and pyromellitic acid. Succinic acid, glutaric acid, adipic acid, sebacic acid, lactic acid, phthalic acid, terephthalic acid, isophthalic acid, trimellitic acid and pyromellitic acid are preferred. Succinic acid, glutaric acid and adipic acid are particularly preferred.

Furthermore, the group of the polycarboxylic acids also encompasses hydroxycarboxylic acids or their internal anhydrides, such as e.g. caprolactone, lactic acid, hydroxybutyric acid, ricinoleic acid etc. Monocarboxylic acids are also included, in particular those having more than 10 C atoms, such as soy oil fatty acid, palm oil fatty acid and ground nut oil fatty acid, wherein their proportion in the overall reaction mixture synthesising the polyether-ester polyol does not exceed 10 wt. % and, in addition, the lower functionality associated therewith is balanced out by the simultaneous use of at least trifunctional polyols, whether on the side of the low molecular weight or the high molecular weight polyols.

The production of the polyether-ester polyols preferably takes place according to the prior art at an elevated temperature in the range of 120 to 250° C., initially under standard pressure and later with the application of a vacuum of 1 to 100 mbar, preferably, but not necessarily, using an esterification or transesterification catalyst, the reaction being completed until the acid value falls to values of 0.05 to 10 mg KOH/g, preferably 0.1 to 3 mg KOH/g and particularly preferably 0.15 to 2.5 mg KOH/g.

Furthermore, within the standard pressure phase before applying a vacuum, an inert gas can be used. Alternatively, of course, or for individual phases of the esterification, liquid or gaseous entrainers can be employed. For example, the water of reaction can be removed using nitrogen as carrier gas in the same way as with the use of an azeotropic entrainer, such as e.g. benzene, toluene, xylene, dioxane, etc.

Mixtures of polyether polyols with polyester polyols can, of course, also be used in any ratios.

Polyether polyols are preferably polyalkylene oxide polyethers based on ethylene oxide and optionally propylene oxide.

These polyether polyols are preferably based on di- or polyfunctional starter molecules such as di- or polyfunctional alcohols or amines.

Examples of these starters are water (regarded as a diol), ethylene glycol, propylene glycol, butylene glycol, glycerol, TMP, sorbitol, pentaerythritol, triethanolamine, ammonia or ethylenediamine.

Polycarbonates comprising hydroxyl groups, preferably polycarbonate diols, with number average molecular weights $M_n$ of 400 to 8000 g/mol, preferably 600 to 3000 g/mol, can also be used. These are obtainable by reaction of carbonic acid derivatives, such as diphenyl carbonate, dimethyl carbonate or phosgene, with polyols, preferably diols.

Examples of these diols are ethylene glycol, 1,2- and 1,3-propanediol, 1,3- and 1,4-butanediol, 1,6-hexanediol, 1,8-octanediol, neopentyl glycol, 1,4-bishydroxymethyl cyclohexane, 2-methyl-1,3-propanediol, 2,2,4-trimethyl-1,3-pentanediol, dipropylene glycol, polypropylene glycols, dibutylene glycol, polybutylene glycols, bisphenol A and lactone-modified diols of the above-mentioned type in question.

For producing the prepolymer A), the polyisocyanate A1) can be reacted with the polyol A2) in an NCO/OH ratio of preferably 4:1 to 12:1, particularly preferably 8:1, and then the content of unreacted polyisocyanates can be separated off by suitable methods. Thin layer distillation is generally used for this purpose, obtaining prepolymers with residual monomer contents of less than 1 wt. %, preferably less than 0.1 wt. %, most particularly preferably less than 0.03 wt. %.

During the production, stabilisers such as benzoyl chloride, isophthaloyl chloride, dibutyl phosphate, 3-chloropropionic acid or methyl tosylate may optionally be added.

The reaction temperature during the production of the prepolymers A) here is preferably 20 to 120° C. and more preferably 60 to 100° C.

The prepolymers that are produced have an average NCO content, measured in accordance with DIN EN ISO 11909, of 2 to 10 wt. %, preferably 2.5 to 8 wt. %.

According to another embodiment of the polyurea system according to the invention, the prepolymers A) can have an average NCO functionality of 1.5 to 2.5, preferably of 1.6 to 2.4, more preferably of 1.7 to 2.3, most particularly preferably of 1.8 to 2.2 and in particular of 2.

As a development of the invention, it is provided that the polyurea system additionally encompasses organic fillers C). These can in particular have a viscosity measured in accordance with DIN 53019 at 23° C. in the range of 10 to 20,000 mPas, preferably of 50 to 4000 mPas and particularly preferably of 50 to 2000 mPas.

The organic fillers of component C) can preferably be hydroxy-functional compounds, in particular polyether polyols.

It is also advantageous if the fillers of component C) have an average OH functionality of 1.5 to 3, preferably of 1.8 to 2.2 and particularly preferably of 2.

For example, polyethylene glycols that are liquid at 23° C., such as PEG 200 to PEG 600, their mono- or dialkyl ethers, such as PEG 500 dimethyl ether, liquid polyether and polyester polyols, liquid polyesters, such as e.g. Ultramoll (Lanxess AG, Leverkusen, DE), as well as glycerol and its liquid derivatives, such as e.g. triacetin (Lanxess AG, Leverkusen, DE), can be used as organic fillers C).

In another preferred embodiment of the polyurea system according to the invention, polyethylene glycols are used as organic fillers. These preferably have a number average molecular weight of 100 to 1000 g/mol and particularly preferably of 200 to 400 g/mol.

To reduce the average equivalent weight of the total compounds used for prepolymer crosslinking further, based on the NCO-reactive groups, it is possible additionally to produce reaction products of the prepolymers A) with the amino-functional compound B) and/or the organic fillers C), in so far as these are amino- or hydroxy-functional, in a separate preliminary reaction and then to use them as a higher molecular weight hardener component.

Preferably during the pre-extension, ratios of isocyanate-reactive groups to isocyanate groups of 50:1 to 1.5:1, particularly preferably 15:1 to 4:1 are established.

An advantage of this modification by pre-extension is that the equivalent weight and the equivalent volume of the hardener component can be modified within relatively broad limits. As a result, commercially available 2-chamber metering systems can be used for application in order to obtain a system that can be adjusted to the desired ratio of NCO-reactive groups to NCO groups with existing ratios of the chamber volumes.

It is, of course, also possible to introduce into the polyurea systems pharmacologically active substances, such as analgesics with and without an anti-inflammatory action, antiphlogistics, antimicrobially active substances, antimycotics or antiparasitically active substances as component D).

The polyurea system according to the invention can be obtained by mixing the prepolymers A) with the amino-functional compound B) and optionally components C) and D). The ratio of free or blocked amino groups to free NCO groups in this case is preferably 1:1.5, particularly preferably 1:1.

The polyurea system according to the invention is particularly suitable for closing, binding, bonding or covering cell tissue and in particular for stopping the discharge of blood or tissue fluids or closing leaks in cell tissue. Most particularly preferably, it can be used for the use or for the production of an agent for closing, binding, bonding or covering human or animal cell tissue. Rapidly curing, transparent, flexible and biocompatible adhesive joints with strong adhesion to the tissue can be produced therewith.

The invention also provides a metering system with two chambers for a polyurea system according to the invention, in which component A) is comprised in one chamber and components B) and optionally components C) and D) of the polyurea system in the other chamber. A metering system of this type is particularly suitable for applying the polyurea system on to tissue as an adhesive.

The invention is explained in more detail below based on examples.

EXAMPLES

Methods

Molecular weights were determined as follows by gel permeation chromatography (GPC): calibration took place using polystyrene standards with molecular weights of Mp 1,000,000 to 162. Tetrahydrofuran p.a. was used as eluent. The following parameters were maintained during the double measurement: degassing: online degasser; throughput: 1 ml/min; analysis time: 45 minutes; detectors: refractometer and UV detector; injection volume: 100 μl-200 μl. The calculation of the average molar mass values Mw; Mn and Mp and the polydispersity Mw/Mn took place using software. Baseline points and evaluation limits were determined in accordance with DIN 55672 Part 1.

NCO contents were determined volumetrically according to DIN-EN ISO 11909 unless otherwise specified.

Viscosities were determined according to ISO 3219 at 23° C.

Residual monomer contents were determined according to DIN ISO 17025.

NMR spectra were determined using a Bruker DRX 700 instrument.

Substances

HDI: hexamethylene diisocyanate (Bayer MaterialScience AG)

All other chemicals were obtained from Aldrich and Fluka.

Synthesis of triethyl-11-methyl-4-oxo-3-oxa-7,11,15-triazaheptadecane-6,16,17-tricarboxylate (1)

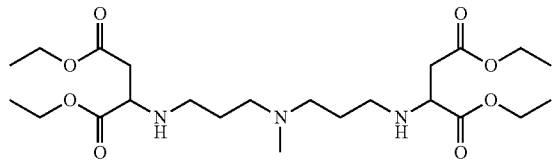 [SMILES: CCOC(=O)CC(NCCCN(C)CCCNC(CC(=O)OCC)C(=O)OCC)C(=O)OCC]

20.66 g (0.12 mol) maleic acid diethyl ester were added to 8.7 g (0.06 mol) N,N'bis(aminopropyl)methylamine. The reaction mixture was stirred for 3 days at 60° C. The product was obtained quantitatively as a yellow liquid.

$^1$H-NMR (CDCl$_3$, 700 MHz): δ=1.29 (t, 12H), 1.67 (t, 4H), 1.89 (br, 2NH), 2.2 (s, 3H) 2.34 (t, 4H), 2.51 (m, 2H), 2.6 (m, 2H), 2.7 (m, 4H), 3.60 (t, 2H), 4.13 (q, 4H), 4.18 (q, 4H).

$^{13}$C-NMR (CDCl$_3$, 700 MHz): 13.9, 27.5, 37.9, 41.9, 46.3, 55.6, 57.6, 60.4, 60.7, 170.6, 173.4.

Synthesis of triethyl-4-oxo-3-oxa-7,14,21-triazatricosane-6,22,23-tricarboxylate (2)

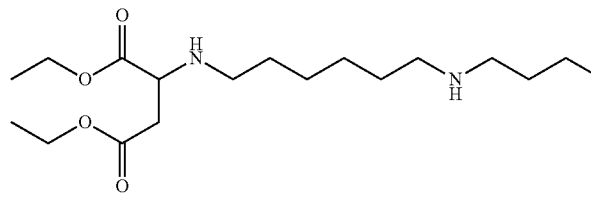

As in (2), 400 g of the product were obtained as a yellow liquid from 154 g (0.72 mol) bis(hexamethylene)triamine and 246 g (1.42 mol) maleic acid diethyl ester.

$^1$H-NMR (CDCl$_3$, 700 MHz): δ=1.27 (t, 6H), 1.29 (t, 6H), 1.34 (m, 8H), 1.49 (br, 3NH), 2.59 (m, 12H), 3.70 (t, 2H), 4.11 (q, 4H), 4.2 (q, 4H).

$^{13}$C-NMR (CDCl$_3$, 700 MHz): 14.1, 26.8, 27.1, 30.0, 30.1, 38.1, 47.9, 50.1, 57.8, 60.3, 60.8, 170.7, 172.7.

Tetraethyl-2,2'-[(2-methylpentane-1,5-diyl)diimino]dibutanedioate (3)

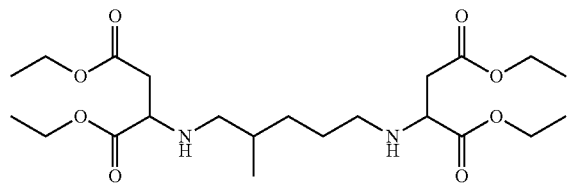 [SMILES: CCOC(=O)CC(NCCCC(C)CNC(CC(=O)OCC)C(=O)OCC)C(=O)OCC]

1 mol 2-methyl-1,5-diaminopentane was slowly added dropwise to 2 mol diethyl maleate under a nitrogen atmosphere, so that the reaction temperature did not exceed 60° C. Heating was then performed to 60° C. until no more diethyl maleate could be detected in the reaction mixture. The product was obtained quantitatively as a yellow liquid.

$^1$H-NMR (CDCl$_3$, 700 MHz): δ=0.89 (d, 3H), 1.11 (m, 1H), 1.27 (t, 6H), 1.32 (t, 6H), 1.4 (m, 4H), 1.5 (br, 2NH), 2.51 (m, 8H), 3.6 (m, 2H), 4.18 (m, 4H), 4.26 (q, 4H),

Synthesis of Prepolymer A 465 g HDI and 2.35 g benzoyl chloride were initially charged in a 1 l four-necked flask. Within 2 h at 80° C., 931.8 g of a trifunctional polyether with a molar mass of 4500, started on glycerol and having an ethylene oxide content of 71% and a propylene oxide content of 29%, based in each case on the total alkylene oxide content, were added and stirring was continued for 1 h. The excess HDI was then distilled off by thin layer distillation at 130° C. and 0.13 mbar. 980 g (71%) of the prepolymer were obtained with an NCO content of 2.37% and a viscosity of 4500 mPas/23° C. The residual monomer content was <0.03% HDI.

Synthesis of Prepolymer B 263 g (1.8 mol) adipic acid were heated to 235° C. with 1591.5 g polyethylene glycol 600 (2.6 mol), with stirring. The resulting water was distilled off over 8.5 h. 100 ppm tin(II) chloride were then added and the mixture was heated for a further 9 h in vacuo (15 mbar) in a water separator to 235° C.

672 g HDI (4 mol) were initially charged with 0.1 wt. % benzoyl chloride and heated to 80° C. 788 g of the previously produced polyester were then metered in over 1 h with stirring, and stirring was continued at 80° C. until a constant NCO content was reached. The excess HDI was removed at 140° C. and 0.13 mbar using a thin layer evaporator. The prepolymer that was obtained had an NCO content of 3.5% and a viscosity of 4700 mPas/23° C. The residual monomer content was <0.03% HDI.

Production of the Tissue Adhesive 4 g of the respective prepolymer were stirred well with an equivalent quantity of the mixture of 1 with the triethyl-4-oxo-3-oxa-7,14,21-triazatricosane-6,22,23-tricarboxylate 2 described in BMS 111002 and with tetraethyl-2,2'-[(2-methylpentane-1,5-diyl)diimino]dibutanedioate 3 respectively in a beaker. Immediately afterwards, the polyurea system was applied as a thin layer on to the muscle tissue to be bonded. The time within which the adhesive system still possessed a sufficiently low viscosity to be able to be applied on to the tissue without any problems was determined as the pot life.

| | Hardener | Ratio of hardeners | Pot life [s] |
|---|---|---|---|
| Prepolymer A (HXH 100) | 3 pure | / | 240 |
| Prepolymer A | 3 with 1 | 0.9:0.1 | 108 |
| Prepolymer A | 3 with 1 | 0.80:0.20 | 60 |
| Prepolymer A | 3 with 1 | 0.70:0.30 | 45 |
| Prepolymer A | 3 with 1 | 0.60:0.40 | 20 |
| Prepolymer A | 3 with 1 | 0.50:0.50 | 20 |
| Prepolymer B | 2 | / | 120 |
| Prepolymer B | 2 with 1 | 0.90:0.10 | 82 |
| Prepolymer B | 2 with 1 | 0.80:0.20 | 60 |
| Prepolymer B | 2 with 1 | 0.70:0.30 | 35 |
| Prepolymer B | 2 with 1 | 0.60:0.40 | 29 |
| Prepolymer B | 2 with 1 | 0.50:0.50 | 20 |

The results listed in the above table show that the polyurea systems according to the invention have a very high rate of curing. In addition, the systems also possess a good adhesive performance. Since the systems according to the invention also comprise no low molecular weight amines that are not incorporated into the polymer network, there is also no risk of such compounds being able to be eluted and thus released in the body.

The invention claimed is:

1. A polyurea system comprising as component A) an isocyanate-functional prepolymer obtained by reacting an aliphatic isocyanate A1) with a polyol A2), and as component B) an amino-functional compound of general formula (I)

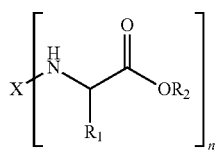

in which

X is a residue of formula (II)

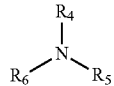

wherein $R_4$, $R_5$, $R_6$ are, each independently of one another or simultaneously, a methyl, ethyl, propyl or butyl residue, having no Zerewitinoff active hydrogen, wherein at least two of $R_4$, $R_5$, $R_6$ are a methylene, ethylene, propylene, or butylene residue, having no Zerewitinoff active hydrogen, $R_1$ is a linear or branched C1 to C4 alkyl residue, a cyclopentyl or cyclohexyl residue, H, or a $CH_2$—$COOR_3$ residue, in which $R_3$ is an organic residue having no Zerewitinoff active hydrogen, $R_2$ is a linear or branched C1 to C10 organic residue having no Zerewitinoff active hydrogen, and n is 2 or 3.

2. The polyurea system according to claim 1, wherein the polyol A2) comprise a polyester polyol and/or a polyester-polyether polyol and/or a polyether polyol.

3. The polyurea system according to claim 1, wherein the polyol A2) has a number average molecular weight of from 4000 to 8500 g/mol.

4. The polyurea system according to claim 1, comprising as component C) an organic filler.

5. The polyurea system according to claim 4, wherein the organic filler is a hydroxy-functional compound.

6. The polyurea system according to claim 5, wherein the hydroxy-functional compound is a polyether polyol.

7. The polyurea system according to claim 5, wherein the hydroxy-functional compound has an average OH functionality of 1.5 to 3.

8. The polyurea system according to claim 1, comprising as component D) a pharmacologically active compound.

9. A method for closing, binding, bonding or covering cell tissue comprising utilizing the polyurea system according to claim 1.

10. A metering system comprising two chambers for a polyurea system according to claim 1, wherein one of the chambers comprises component A) and the other chamber comprises component B) and optionally component C) and D).

* * * * *